(12) United States Patent
Walter et al.

(10) Patent No.: US 10,912,940 B2
(45) Date of Patent: Feb. 9, 2021

(54) CONNECTION JOINTS FOR JOINING WIRES AND PADS CONSTRUCTED OF DIFFERENT CONDUCTIVE MATERIALS AND METHODS OF MAKING THE SAME

(71) Applicant: Advanced Bionics AG, Staefa (CH)

(72) Inventors: Jeryle L. Walter, Valencia, CA (US); Enrique Gandaria, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 152 days.

(21) Appl. No.: 16/125,628

(22) Filed: Sep. 7, 2018

(65) Prior Publication Data
US 2019/0091473 A1    Mar. 28, 2019

Related U.S. Application Data

(60) Provisional application No. 62/562,147, filed on Sep. 22, 2017.

(51) Int. Cl.
*B23K 1/00*    (2006.01)
*A61N 1/36*    (2006.01)
(Continued)

(52) U.S. Cl.
CPC ......... *A61N 1/36038* (2017.08); *A61N 1/375* (2013.01); *B23K 1/0008* (2013.01); *B23P 23/04* (2013.01); *H01R 4/023* (2013.01); *H01R 4/62* (2013.01); *H01R 12/53* (2013.01); *H01R 43/00* (2013.01); *A61N 1/0541* (2013.01);
(Continued)

(58) Field of Classification Search
CPC .. A61N 1/36038; A61N 1/375; A61N 1/3752; A61N 1/0541; H01R 4/023; H01R 12/53; H01R 4/62; H01R 43/00; H01R 12/51; B23P 23/04; B23K 1/00–206; B23K 20/004; B23K 2101/22; B23K 2101/32–42
USPC .... 228/56.3, 245–255, 179.1–180.22, 180.5, 228/4.5, 904
See application file for complete search history.

(56) References Cited

U.S. PATENT DOCUMENTS 3,384,958 A * 5/1968 Christian ............. B23K 35/001
29/829
3,463,898 A * 8/1969 Okabe .................. B23K 26/067
219/121.63
(Continued)

*Primary Examiner* — Kiley S Stoner
(74) *Attorney, Agent, or Firm* — ALG Intellectual Property, LLC

(57) ABSTRACT

An exemplary connection joint includes a wire constructed from a first conductive material having a first melting point and a pad constructed from a second conductive material different from the first conductive material and having a second melting point lower than the first melting point. The connection joint further includes a groove within the pad that partially surrounds the wire and a fixative covering the wire and the pad so as to fix the wire in place within the groove. The groove is formed by a displacement of the second conductive material that occurs when the wire is in contact with the pad at a contact area of the pad that is heated to a temperature between the first and second melting points so as to reflow the second conductive material from which the pad is constructed without reflowing the first conductive material from which the wire is constructed.

20 Claims, 9 Drawing Sheets

(51) Int. Cl.
  *H01R 4/62*   (2006.01)
  *B23P 23/04*  (2006.01)
  *H01R 43/00*  (2006.01)
  *H01R 4/02*   (2006.01)
  *H01R 12/53*  (2011.01)
  *A61N 1/375*  (2006.01)
  *H01R 12/51*  (2011.01)
  *A61N 1/05*   (2006.01)
  *B23K 101/36* (2006.01)
  *B23K 101/32* (2006.01)

(52) U.S. Cl.
  CPC ........ *A61N 1/3752* (2013.01); *B23K 2101/32* (2018.08); *B23K 2101/36* (2018.08); *H01R 12/51* (2013.01)

(56) References Cited

U.S. PATENT DOCUMENTS

| | | | | |
|---|---|---|---|---|
| 3,520,053 A * | 7/1970 | Hinton | ................. | H05B 3/84 29/611 |
| 3,665,589 A * | 5/1972 | Farrell | ............. | H01L 21/67138 228/199 |
| 3,672,047 A * | 6/1972 | Sakamoto | ............ | B23K 20/005 29/854 |
| 4,396,140 A * | 8/1983 | Jaffe | ................. | H05K 3/3426 228/122.1 |
| 4,451,968 A * | 6/1984 | Jensen | ................. | H01L 24/80 136/250 |
| 4,700,044 A * | 10/1987 | Hokanson | ............ | B23K 1/0056 219/121.63 |
| 4,907,734 A * | 3/1990 | Conru | ................. | B23K 20/023 228/110.1 |
| 4,948,030 A * | 8/1990 | Chason | ................. | B23K 1/20 228/118 |
| 5,298,715 A | 3/1994 | Chalco et al. | | |
| 5,639,696 A * | 6/1997 | Liang | ................. | H01L 21/4853 228/180.22 |
| 6,027,008 A * | 2/2000 | Toi | ................. | B23K 20/023 228/110.1 |
| 6,119,924 A * | 9/2000 | Toi | ................. | B23K 20/023 228/179.1 |
| 7,225,538 B2 * | 6/2007 | Eldridge | ............. | B23K 20/004 228/180.5 |
| 7,489,041 B2 * | 2/2009 | Akram | ............. | H01L 23/53238 257/778 |
| 8,485,418 B2 * | 7/2013 | Eldridge | ............. | B23K 20/004 228/179.1 |
| 9,035,214 B2 * | 5/2015 | Morimoto | ............ | B23K 1/0056 219/121.64 |
| 2007/0228110 A1 * | 10/2007 | Eldridge | ............. | H01L 21/6715 228/180.5 |
| 2015/0222070 A1 * | 8/2015 | Morimoto | ............ | H01F 41/10 29/860 |
| 2015/0228378 A1 | 8/2015 | Guetig et al. | | |

* cited by examiner

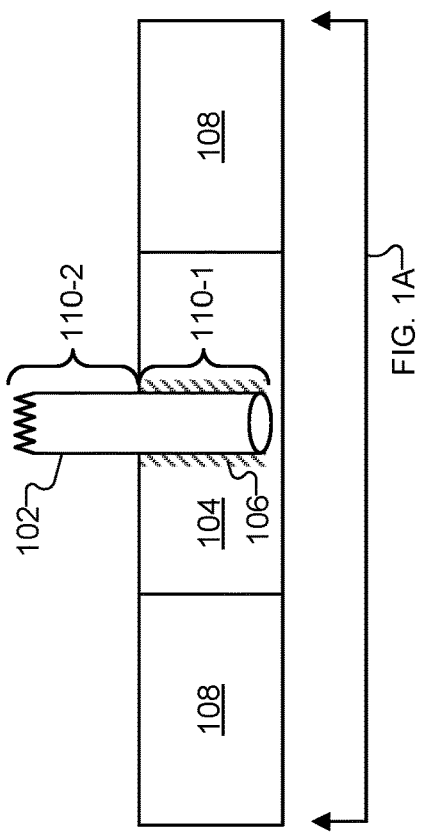
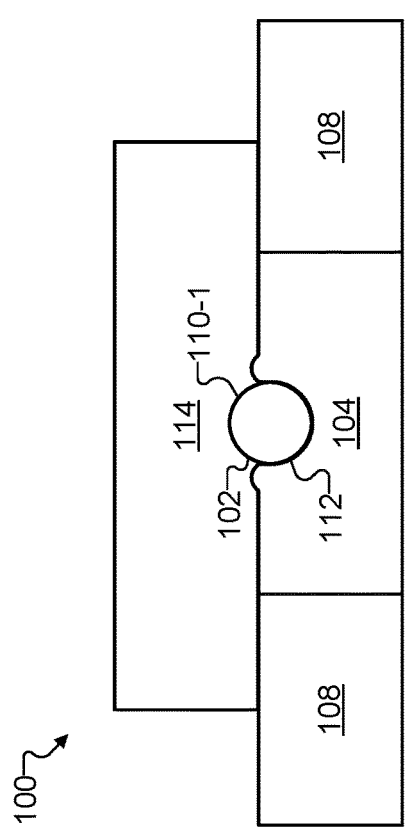
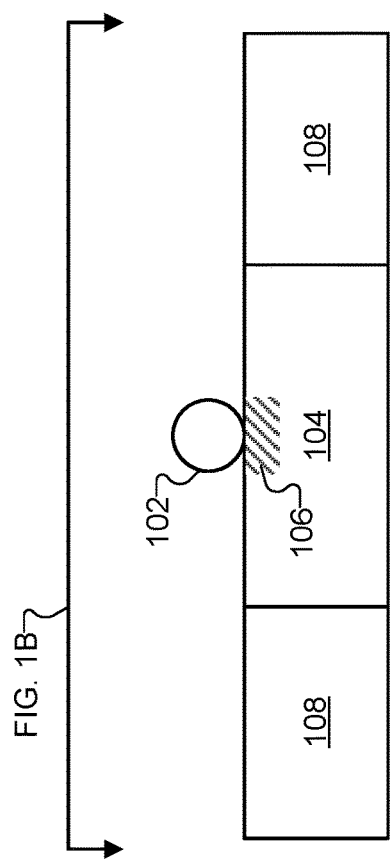
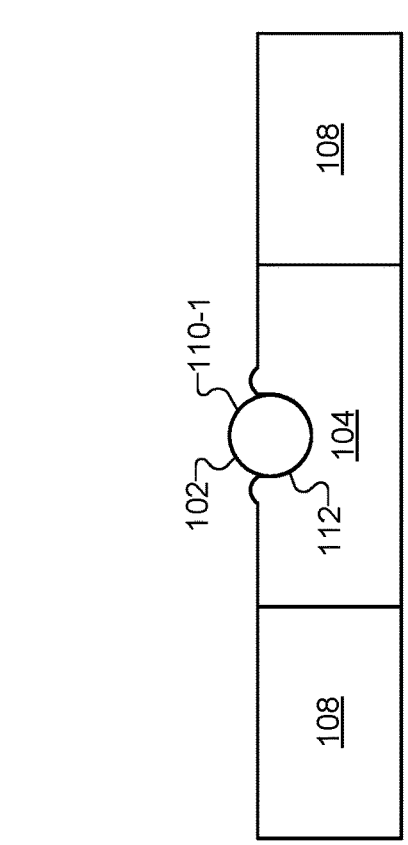

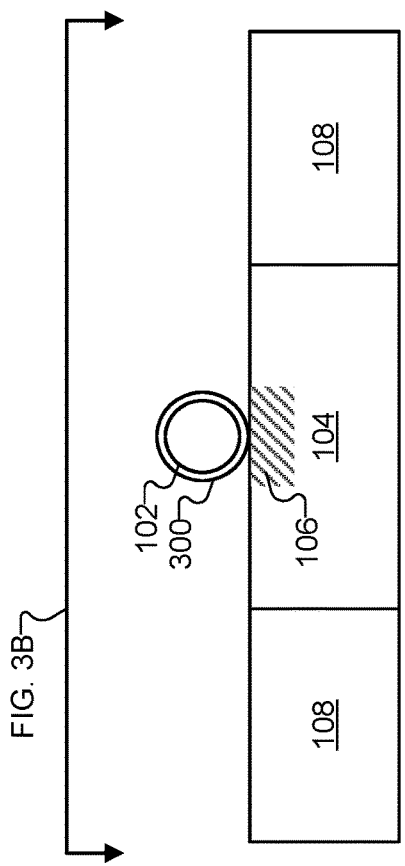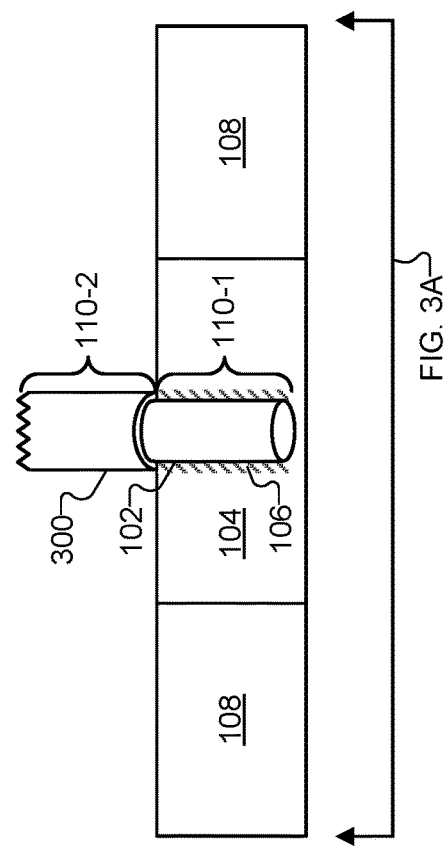

CONNECTION JOINTS FOR JOINING WIRES AND PADS CONSTRUCTED OF DIFFERENT CONDUCTIVE MATERIALS AND METHODS OF MAKING THE SAME

RELATED APPLICATIONS

The present application claims priority under 35 U.S.C. § 119(e) to U.S. Provisional Patent Application No. 62/562,147, filed on Sep. 22, 2017, and entitled "Connection Joints for Joining Wires and Pads Constructed of Different Conductive Materials and Methods of Making the Same," the contents of which are hereby incorporated by reference in their entirety.

BACKGROUND INFORMATION

Various materials such as metals and thermoplastics may be joined together using welding techniques whereby both materials are heated to a melting point and, while in a reflowed state (i.e., a liquid state) at a temperature above the melting point, mixed together such that the materials become fused to one another when cooled back down to a solid state. In this way, a sturdy connection (e.g., a welding joint) between the materials may be formed.

Typically (e.g., whenever possible), welding techniques are employed to join two like materials (e.g., like alloys with similar or identical constituent elements, blends, geometries, etc.). Like materials may facilitate welding techniques for various reasons such as because the materials have a same melting point, the materials readily mix together when reflowed so as to form strong connection joints, and so forth. However, in certain situations, it may be desirable to join dissimilar materials (i.e., different materials having different melting points, constituent elements, blends, geometries, and/or other differences). For example, in certain designs that require materials to be joined, various design constraints and requirements (e.g., component costs, component availability, biocompatibility requirements, etc.) may render it undesirable, inconvenient, or reasonably impossible (e.g., prohibitively expensive) to design in like materials for the materials that need to be joined. As such, dissimilar materials may be employed in the designs, but it may be difficult, impractical, inconvenient, or reasonably impossible to join the dissimilar materials using welding joints formed using conventional welding techniques.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 1A-1D illustrate how an exemplary connection joint for joining a wire and a pad constructed of different conductive materials may be formed according to principles described herein.

FIGS. 3A-3B illustrate how the connection joint of FIG. 1D may be formed when the wire being joined to the pad is sheathed by an insulative material according to principles described herein.

DETAILED DESCRIPTION

Figure 2:
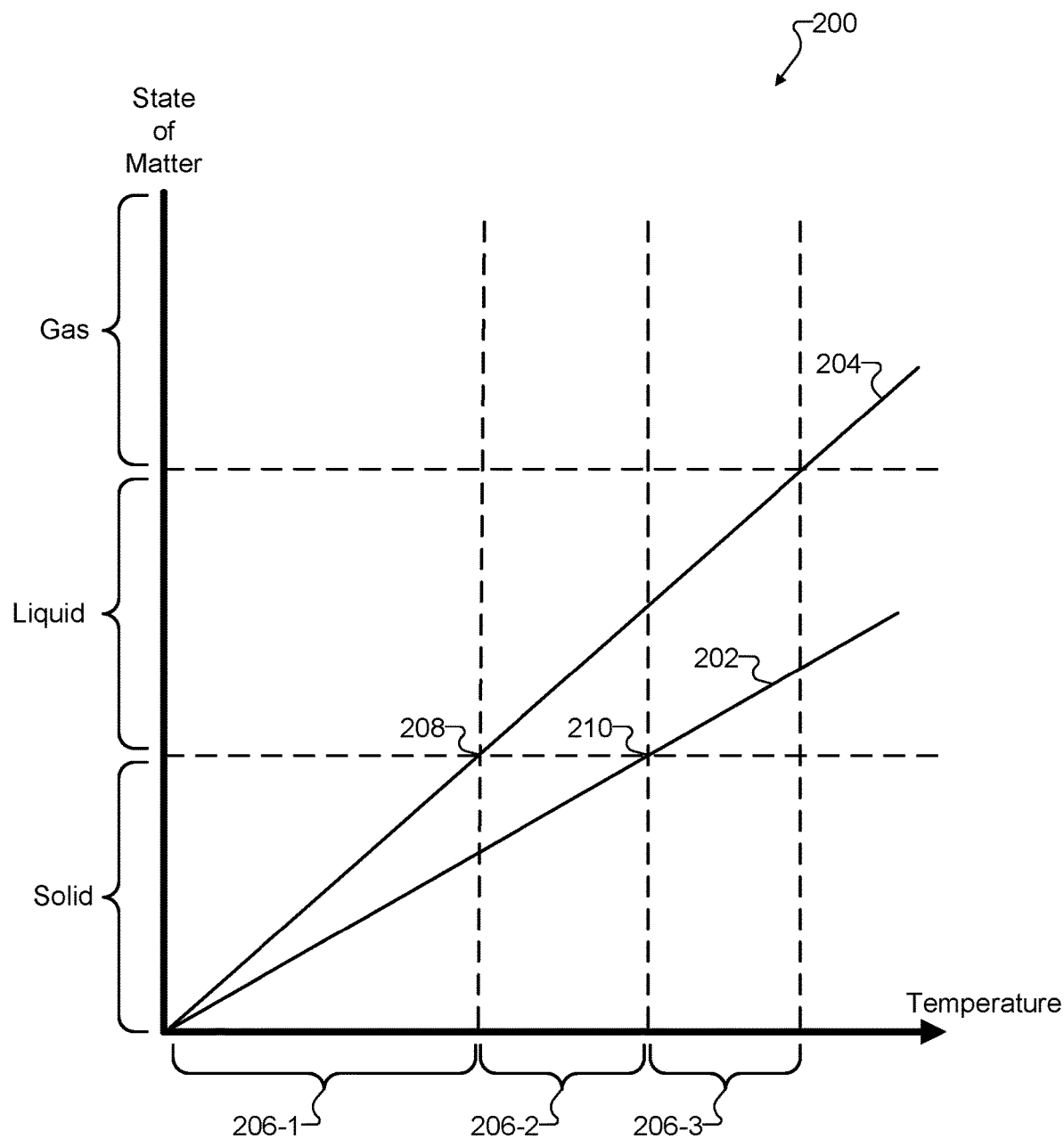
FIG. 2 illustrates exemplary temperature-state profiles for different conductive materials that may be joined in the connection joint of FIG. 1D according to principles described herein.

Connection joints for joining wires and pads constructed of different conductive materials and methods of making or forming such connection joints are described herein. As described above, conventional welding techniques may be fusion-based in that they may involve bringing both materials that are to be joined to a temperature above a melting point of the materials such that the materials may mix together while in a reflowed state so as to be fused to one another after the materials are cooled. However, as further described above, when the materials to be joined are dissimilar (e.g., have different melting points and/or other different characteristics), conventional, fusion-based welding techniques may be challenging or impractical for various reasons. Accordingly, to overcome the challenges of fusion-based welding techniques for joining dissimilar materials, a non-fusion-based connection joint for joining dissimilar materials without the materials mixing together while both in a liquid state will be disclosed herein, along with methods for making such a connection joint.

In one implementation, a non-fusion-based connection joint such as described above may include a wire constructed from a first conductive material (e.g., an elemental metal, an alloy, etc.) having a first melting point, and may further include a pad constructed from a second conductive material (e.g., a conductive material different from the first conductive material) having a second melting point lower than the first melting point. The connection joint may also include a groove within the pad and that partially surrounds a first segment of the wire (e.g., a tip of the wire). For example, the groove may be formed by a displacement of the second conductive material of the pad that occurs when both: 1) the first segment of the wire is in contact with the pad at a contact area of the pad, and 2) the contact area is heated to a temperature between the second melting point and the first melting point so as to reflow the second conductive material from which the pad is constructed without reflowing the first conductive material from which the wire is constructed. The connection joint may further include a fixative (e.g., an epoxy coating or the like)

covering the first segment of the wire and at least a portion of the pad so as to fix the first segment of the wire in place within the groove.

Non-fusion-based connection joints for joining wires and pads constructed of different conductive materials such as described above may be useful in various applications. For instance, certain medical device designs may have strict constraints (e.g., biocompatibility constraints, reliability constraints, etc.) that severely limit the components that may be used in the designs. In some cases, these limitations may result in designs that call for dissimilar materials to be joined together. For example, available wires to be included within an electrode lead may be constructed of a platinum-iridium alloy while available pads on a feedthrough assembly of an implanted medical device to which the wires of the electrode lead are to be connected may be constructed of pure platinum. If it is not possible, practical, or cost efficient to use wires and pads constructed of like materials (e.g., identical materials, materials having a same melting point, etc.), these dissimilar materials of the wires and pads may be joined using non-fusion-based connection joints described herein.

By way of a more specific example, a medical device configured to be implanted within a patient may include electronic circuitry, a housing enclosing the electronic circuitry and that is biocompatible and hermetically sealed, and a feedthrough assembly of the housing including a via upon which a pad is disposed external to the housing. In this example, the feedthrough assembly may be configured to conduct (e.g., by way of the via) electrical signals to and from the electronic circuitry enclosed within the housing and an electrode included on an electrode lead coupled with the medical device by way of the pad. The electrode lead may include a wire constructed from a first conductive material (e.g., a platinum-iridium alloy material) having a first melting point, while the pad may be constructed from a second conductive material different from the first conductive material (e.g., a pure platinum material) and having a second melting point lower than the first melting point.

In this example, a first segment of the wire may be coupled to the pad by being partially surrounded by a groove within the pad. For instance, the groove may have been formed by a displacement of the second conductive material that occurred when the first segment of the wire was in contact with the pad at a contact area of the pad and the contact area was heated to a temperature between the second melting point and the first melting point so as to reflow the second conductive material from which the pad is constructed without reflowing the first conductive material from which the wire is constructed. The first segment of the wire may be further coupled to the pad by being covered by a fixative covering the first segment of the wire and at least a portion of the pad so as to fix the first segment of the wire in place within the groove.

Whether used for medical devices such as described above or in other types of applications where designs call for dissimilar materials to be joined together, the connection joints for joining wires and pads constructed of different conductive materials and methods for making them described herein may provide various benefits. For example, these connection joints may be used to join materials that meet various constraints of availability, biocompatibility, strength and other inherent characteristics, cost, and so forth. As such, designers may benefit from increased flexibility in the materials they may use in their designs, and may not be forced to design in less ideal materials (e.g., materials that have undesirable characteristics, lack desirable characteristics, are more costly, have less availability, etc.) merely based on a difficulty of joining the materials based on conventional fusion-based welding techniques. At the same time, designers who employ the non-fusion-based connection joints described herein may not be forced to compromise on the strength, quality, robustness, ease of implementation, associated costs, or other qualities of the connection joints themselves. For example, the connection joints described herein may be formed using off-the-shelf equipment and may not require a dedicated welding machine for making a special fusion-based weld of the dissimilar materials.

Another benefit of the connection joints for joining wires and pads constructed of different conductive materials described herein is that no neckdown may be formed on the final connection joint due to the fact that the conductive material from which the wire itself is constructed is never heated sufficiently to reflow. As a result, non-fusion-based connection joints formed using the methods described herein may actually be stronger and more robust than a conventional fusion-based weld in certain examples. Additionally, as will be described in more detail below, connection joints described herein may conveniently and accurately remove insulation from appropriate segments of wires, saving technicians from having to strip insulation from the segments of wires using other less convenient and/or less accurate methods (e.g., using lasers, open flames, etc.).

Various embodiments will now be described in more detail with reference to the figures. The disclosed systems and methods may provide one or more of the benefits mentioned above and/or various additional and/or alternative benefits that will be made apparent herein.

FIGS. 1A-1D illustrate how an exemplary connection joint for joining a wire and a pad constructed of different conductive materials may be formed. More particularly, FIGS. 1A-1C illustrate intermediate steps for forming a connection joint 100 that is shown in final form in FIG. 1D. It will be understood that the elements shown in FIGS. 1A-1D are exemplary only and, as such, may not be drawn to scale and/or may omit or exaggerate certain details.

First, FIGS. 1A and 1B illustrate, from side and top views, respectively, how a wire and a pad may be positioned in order to make connection joint 100. Specifically, a wire 102 (e.g., a wire constructed from a first conductive material having a first melting point) may be positioned with respect to a pad 104 (e.g., a pad constructed from a second conductive material different from the first conductive material and having a second melting point lower than the first melting point) such that wire 102 is positioned at a particular contact area 106 of pad 104. As illustrated, pad 104 may be surrounded by another material 108 such as an insulative ceramic material or the like. For example, if pad 104 is disposed within a printed circuit board ("PCB"), material 108 may represent non-conductive substrate material of the PCB surrounding pad 104.

The first and second conductive materials from which wire 102 and pad 104 are constructed, respectively, may be any conductive materials as may serve a particular implementation. For example, the materials may be any suitable metals (e.g., pure elemental metals such as platinum, copper, etc.), alloys (i.e., elemental metals blended together so as to give the alloy certain characteristics of each of the constituent elements in the blend), and/or other suitable conductive materials capable of carrying a current and being joined together to form a connection joint as described herein. In certain examples where connection joint 100 is to be used on a medical device configured to be implanted within a patient, the first and second conductive materials may be biocompatible so as to be suitable for inclusion within the medical device. For example, the first conductive material from which wire 102 is constructed may be a platinum-iridium alloy material (e.g., an 80/20 platinum-iridium blend having a melting point of approximately 1830° C.), while the second conductive material from which pad 104 is constructed may be a pure platinum material (i.e., approximately 100% platinum and having a melting point of approximately 1768° C.). While these materials may be different and have different melting points, making them difficult to weld together using conventional welding techniques, each of these materials may be conductive, biocompatible, and have other characteristics making them particularly suitable for use in constructing wire 102 and pad 104, respectively.

Just as contact area 106 of pad 104, where wire 102 is positioned, may not encompass the entirety of pad 104, it will be understood that only a segment of wire 102, and not the entirety of wire 102, may be positioned over contact area 106 to become part of connection joint 100. Specifically, as illustrated by the top view provided by FIG. 1B, a first segment 110-1 of wire 102 may be in contact with pad 104 at contact area 106, while a second segment 110-2 of wire 102 may not be in contact with pad 104 and may not be included as part of connection joint 100. As shown in FIG. 1B, first segment 110-1 may, in certain examples, be a tip of wire 102. In other examples not explicitly shown, however, it will be understood that first segment 110-1 that is included in connection joint 100 may be a segment that is not at a tip, but, rather, is included in the middle of wire 102. For example, in certain implementations, wire 102 may be connected at two different segments (e.g., a tip and a middle section) to two different pads to form two different connection joints.

Once the positioning has been performed to put segment 110-1 of wire 102 in contact with pad 104 at contact area 106, the respective positions of wire 102 and pad 104 may be maintained temporarily while other operations are performed to form connection joint 100. For example, tape (e.g., KAPTON tape or the like) or other suitable adhesive means may be used to hold segment 110-1 of wire 102 in place on contact area 106 of pad 104 until further steps are performed and/or connection joint 100 is fully formed, after which the temporary positioning support (e.g., tape or the like) may be removed or destroyed (e.g., burned off, etc.).

While segment 110-1 of wire 102 is in contact with pad 104 at contact area 106, contact area 106 of pad 104 may be heated to a temperature between the second melting point (i.e., the melting point of the conductive material of pad 104) and the first melting point (i.e., the melting point of the conductive material of wire 102) so as to reflow the second conductive material from which the pad is constructed without reflowing the first conductive material from which the wire is constructed. As shown in FIG. 1C, this reflowing of the second conductive material may allow segment 110-1 of wire 102 to displace some of the reflowed second conductive material of pad 104 to thereby form a groove 112 within pad 104. As used herein, "grooves" such as groove 112 are formed by pressing (e.g., by applied pressure, gravity, etc.) a non-reflowed material with a relatively high melting point (e.g., wire 102) into a reflowed material with a melting point lower than that of the non-reflowed material (e.g., pad 104). As such, grooves may take any shape, length, aspect ratio, and form as may serve a particular implementation. The characteristics of grooves such as groove 112 are determined by various aspects such as the shape of the non-reflowed material, the orientation of the materials when the pressing occurs, the depth to which the non-reflowed material is pressed within the reflowed material, and so forth. As such, grooves are not to be understood to be limited to require any particular attributes (e.g., including shape, length, aspect ratio, etc.) that may be associated with conventional usage of the term "groove." As shown, groove 112 may partially surround segment 110-1 of wire 102 (e.g., surrounding segment 110-1 of wire 102 along the bottom and sides, but not covering the top of segment 110-1).

Contact area 106 may be heated so as to reflow and allow for the formation of groove 112 in any manner as may serve a particular implementation. For example, part or all of pad 104, including contact area 106, may be heated using a welding system, a reflow soldering system, or the like. For example, pad 104 may be heated using a hot-bar system with a programmed profile configured to heat pad 104 to the desired temperature for a suitable amount of time (e.g., a few hundred milliseconds or the like).

While contact area 106 is heated such that the second conductive material is reflowed, segment 110-1 of wire 102 may sink into, be captured by, be pressed into, or otherwise displace some of the reflowed second conductive material of pad 104 to form groove 112 in any suitable manner. As this occurs, the first conductive material of wire 102 may not be hot enough to reflow and, as such, no fusion or mixing together of the first conductive material and the second conductive material may occur. For example, in certain implementations, pressure may be applied onto segment 110-1 of wire 102 (e.g., by a heating element of a hot-bar system simultaneously heating the area and exerting a downward force on segment 110-1 of wire 102) to force segment 110-1 of wire 102 to partially sink into the reflowed second conductive material of pad 104 so as to displace some of the reflowed second conductive material to form groove 112 within pad 104. In other implementations, pressure may be applied to segment 110-1 of wire 102 in a different way, surface tension of pad 104 at contact area 106 may capture segment 110-1 of wire 102 without pressure being applied to capture segment 110-1, gravity may cause segment 110-1 to sink into the conductive material of pad 104 without pressure being applied to capture segment 110-1, or segment 110-1 of wire 102 may otherwise displace some of the reflowed second conductive material in any other way as may serve a particular implementation.

Subsequent to the contact area being heated, the second conductive material of pad 104 may be allowed to cool until the second conductive material is no longer reflowed (i.e., the material transforms back into a solid state). At this point, as shown in FIG. 1C, segment 110-1 may be situated within groove 112 and, because the first conductive material of segment 110-1 of wire 102 is in contact with and partially surrounded by the second conductive material of pad 104, may form a conductive connection by which current may be readily conducted between pad 104 and wire 102. However, because the first conductive material of wire 102 did not reflow and no fusing of the first and second conductive materials occurred, segment 110-1 of wire 102 may simply be resting in groove 112 and may be subject to removal from groove 112 with minimal force (e.g., inadvertent removal from groove 112 if wire 102 or/or pad 104 were to be accidentally bumped). Thus, in order to cause segment 110-1 of wire 102 to remain joined to and conductively coupled with pad 104 by way of groove 112 more permanently, a fixative covering segment 110-1 of wire 102 and at least a portion of pad 104 may be added so as to fix segment 110-1 of wire 102 in place within groove 112.

To illustrate, as shown in FIG. 1D, a fixative 114 may be applied to fully cover segment 110-1 of wire 102, as well as to cover at least a portion of pad 104 (e.g., all of pad 104 as well as part of material 108 as shown in this example). Fixative 114 may be applied after the second conductive material of pad 104 has cooled (e.g., so as to no longer be reflowed) and while fixative 114 is in a liquid form. Subsequently, fixative 114 may be cured (e.g., oven cured at 120° C. for approximately 30 minutes in certain examples) to change fixative 114 from the liquid form into a solid form.

The substance used for fixative 114 may be any substance capable of holding things rigidly in place and/or sticking them together as may serve a particular implementation. In particular, fixative 114 may be any substance capable of physically fixing a segment of a wire in place within a groove formed within a pad in any of the ways described herein. For example, fixative 114 may be implemented as an epoxy or other material such as a high-durometer polyurethane, silicone, glue, or other adhesive capable of covering at least a portion of pad 104 and rigidly holding wire 102 in place within groove 112. Fixative 114 may be applied to pad 104 in a layer of any thickness as may serve a particular implementation. Additionally, in different implementations, fixative 114 may be applied onto only a portion of pad 104 (e.g., a portion that includes wire 102 and groove 112) or onto an entirety of pad 104 as may be appropriate or convenient.

In certain examples, design requirements may dictate that fixative 114 be biocompatible and suitable for use in a medical device configured to be implanted in a patient. For example, such biocompatible fixatives may be required for designs involving the cochlear implants described herein. As such, fixative 114 may be implemented as a biocompatible epoxy or another such biocompatible fixative. While conductive implementations of fixative 114 may provide advantages such as additional conductivity (e.g., reduced resistance) and/or redundant conductive continuity between wire 102 and pad 104 where their use is possible (e.g., outside of implantable medical devices), many biocompatible fixatives such as biocompatible epoxies are non-conductive. Fortunately, while non-conductive fixatives do not contribute to the conductive continuity between wire 102 and pad 104 in the way conductive fixatives do, the conductive continuity between wire 102 and pad 104 is sufficient even with a non-conductive fixative 114 because the fixative holds wire 102 firmly in place within groove 112 such that direct contact between wire 102 and pad 104 (which partially surrounds wire 102) is maintained.

Once fixative 114 has been cured and is solid, connection joint 100 may be fully formed and may be tested and used. For instance, a continuity test may be performed to ensure current may freely flow (i.e., without an undue amount of resistance) from wire 102 to pad 104, an integrity test may be performed to ensure that the connection of wire 102 to pad 104 meets a particular strength threshold, and so forth.

As described above, to form a connection joint like connection joint 100, a contact area may be heated to a temperature between a lower melting point of a conductive material of which a pad is constructed and a higher melting point of a conductive material of which a wire is constructed so as to reflow the conductive material from which the pad is constructed without reflowing the first conductive material from which the wire is constructed. To illustrate, FIG. 2 shows exemplary temperature-state profiles for different conductive materials that may be joined in connection joint 100. Specifically, as shown, a graph 200 depicting temperature along a horizontal axis and states of matter (i.e., solid, liquid, and gas) along a vertical axis includes a temperature-state profile 202 for the first conductive material of wire 102 and a temperature-state profile 204 for the second conductive material of pad 104.

Three distinct temperature regions 206 (i.e., temperature regions 206-1 through 206-3) are demarcated in graph 200 along the horizontal temperature axis. In a temperature region 206-1, temperature-state profiles 202 and 204 indicate that both the first and second conductive materials of wire 102 and pad 104, respectively, are in a solid state. For instance, temperature region 206-1 may include a natural ambient temperature at which the positioning of wire 102 and pad 104 may be performed (e.g., prior to the heating) and at which a device incorporating the fully formed connection joint 100 may operate.

In a temperature region 206-2, temperature-state profiles 202 and 204 indicate, respectively, that the first conductive material of wire 102 remains in the solid state while the second conductive material of pad 104 has crossed a melting point 208 to transition to a liquid state (i.e., a reflowed state). In temperature region 206-2, segment 110-1 of wire 102 may thus displace some of the second conductive material of pad 104 so as to form groove 112. In other words, in order to form connection joint 100 as described above, contact area 106 of pad 104 may be heated to a temperature that is within temperature region 206-2.

In contrast, temperature region 206-3 may include a temperature at which conventional, fusion-based welding occurs (and that may be too hot to form connection joint 100 according to the methods described herein). As indicated by temperature-state profile 202, the first conductive material from which wire 102 is constructed has crossed a melting point 210 and is, like the second conductive material from which pad 104 is constructed, in a liquid (i.e., reflowed) state in temperature region 206-3. Accordingly, at these temperatures, the first and second conductive materials may mix together and form a fusion-based joint when cooled back to a solid state (e.g., when brought back to a temperature within temperature region 206-1).

In some examples, wire 102 may be covered by a non-conductive sleeve or coating. For example, prior to groove 112 being formed by the heating of contact area 106 and while segment 110-1 of wire 102 is in contact with pad 104 at contact area 106, segments 110-1 and 110-2 of wire 102 may both be sheathed by an insulative material such as PARYLENE, polytetrafluoroethylene ("PTFE") (e.g., TEFLON PTFE polymer), or another insulative material as may serve a particular implementation. The insulative sheath around wire 102 may be included for various reasons such as to protect wire 102, to reduce the risk of inadvertent short circuiting involving wire 102, and/or for other reasons. For example, as will be described and illustrated below, in some examples, a plurality of wires associated with an electrode lead may be included in a plurality of connection joints that are disposed near one another on a feedthrough assembly of a medical device (e.g., a cochlear implant or the like). Due to the proximity of each wire to other wires, short circuiting where exposed wires inadvertently touch other exposed wires to allow current to flow in an unintended way could be likely to occur if each wire is not protected by an insulative covering of some kind.

However, because a conductive connection between a wire and a pad is desirable at a connection joint such as connection joint 100, it may be desirable, prior to completion of the connection joint (e.g., prior to the application of the fixative), for the insulative sheath around the wire to be removed from a first segment of the wire that is in contact with the pad. At the same time, it may also be desirable, when the insulation is removed from the first segment of the wire, for the insulation to remain intact on a second segment of the wire adjacent to the first segment. In other words, to allow for a solid connection to be made at the connection joint while still preventing risk of inadvertent short circuiting and other problems, it may be desirable to remove insulation material only from a portion of the wire contacting the pad and not a portion of the wire that is not contacting the pad.

To illustrate, FIGS. 3A-3B show how connection joint 100 may be formed when wire 102 (i.e., the wire being joined to pad 104) is sheathed by an insulative material. As shown, FIG. 3A includes the same elements as FIG. 1A, except that wire 102 is shown to be covered around the entirety of its circumference by an insulative material 300 (e.g., a PARYLENE material, a PTFE material, etc.). As such, even when segment 110-1 of wire 102 is positioned at contact area 106 as shown, there may be no conductive connection between wire 102 and pad 104 until insulative material 300 is removed from segment 110-1.

As mentioned above, it may be desirable for insulative material 300 to be removed from segment 110-1 only without also being removed from segment 110-2. FIG. 3B illustrates this ideal case. Specifically, from a top view, FIG. 3B shows that segment 110-1 (i.e., the segment of wire 102 that is in contact with pad 104 and will form part of connection joint 100) has had insulative material 300 removed, while segment 110-2 (i.e., the segment of wire 102 adjacent to segment 110-1 that is not in contact with pad 104 and will not form part of connection joint 100) is still sheathed by insulative material 300. Thus, when connection joint 100 is formed by the operations described above (e.g., heating contact area 106, displacing reflowed conductive material of pad 104 to make a groove for segment 110-1 to rest in, applying a fixative to fix segment 110-1 of wire 102 in place within the groove, etc.), a robust and conductive connection joint may be formed while preventing inadvertent short circuiting based on segment 110-2 of wire 102 that is not included within the connection joint.

Insulative material 300 may be removed from segment 110-1 during the making of connection joint 100 in any suitable way. For example, conventional ways of removing insulative material 300 may involve removing the sheath using a precision laser, burning off the insulative material using an open flame, and/or so forth. However, these techniques may be difficult or expensive to implement, as well as may provide less precise control over how much of the insulative material is removed. For example, more insulative material 300 than may be necessary or desirable may be removed from wire 102 using these methods (e.g., including removing part of the sheath from segment 110-2 so as to increase the risk of short circuiting with other wires).

In these or other examples, insulative material 300 may have a boiling point lower than the temperature to which the contact area is heated. Thus, instead of using lasers, open flames, or other such means to remove insulative material 300 from segment 110-1 prior to the positioning of segment 110-1 of wire 102 on contact area 106 of pad 104, insulative material 300 may be burned off of segment 110-1 of wire 102 without also being burned off of segment 110-2 of wire 102 when the groove is formed by the heating of contact area 106. In other words, the same heat (e.g., applied by a welding machine such as a hot bar system or the like) used to heat contact area 106 to reflow the conductive material of pad 104 may also heat insulative material 300 sufficiently to burn off (e.g., melt, boil, vaporize, combust, etc.) the insulative material 300 around segment 110-1. At the same time, because this heat is not applied to segment 110-2 of wire 102, insulative material 300 covering segment 110-2 of wire 102 may remain unaffected. Accordingly, subsequent to the groove being formed by the heating of contact area 106, segment 110-1 of wire 102 (which may now be partially surrounded by the groove) may no longer be sheathed by insulative material 300 while segment 110-2 of wire 102 adjacent to segment 110-1 continues to be sheathed by insulative material 300.

Figure 4:
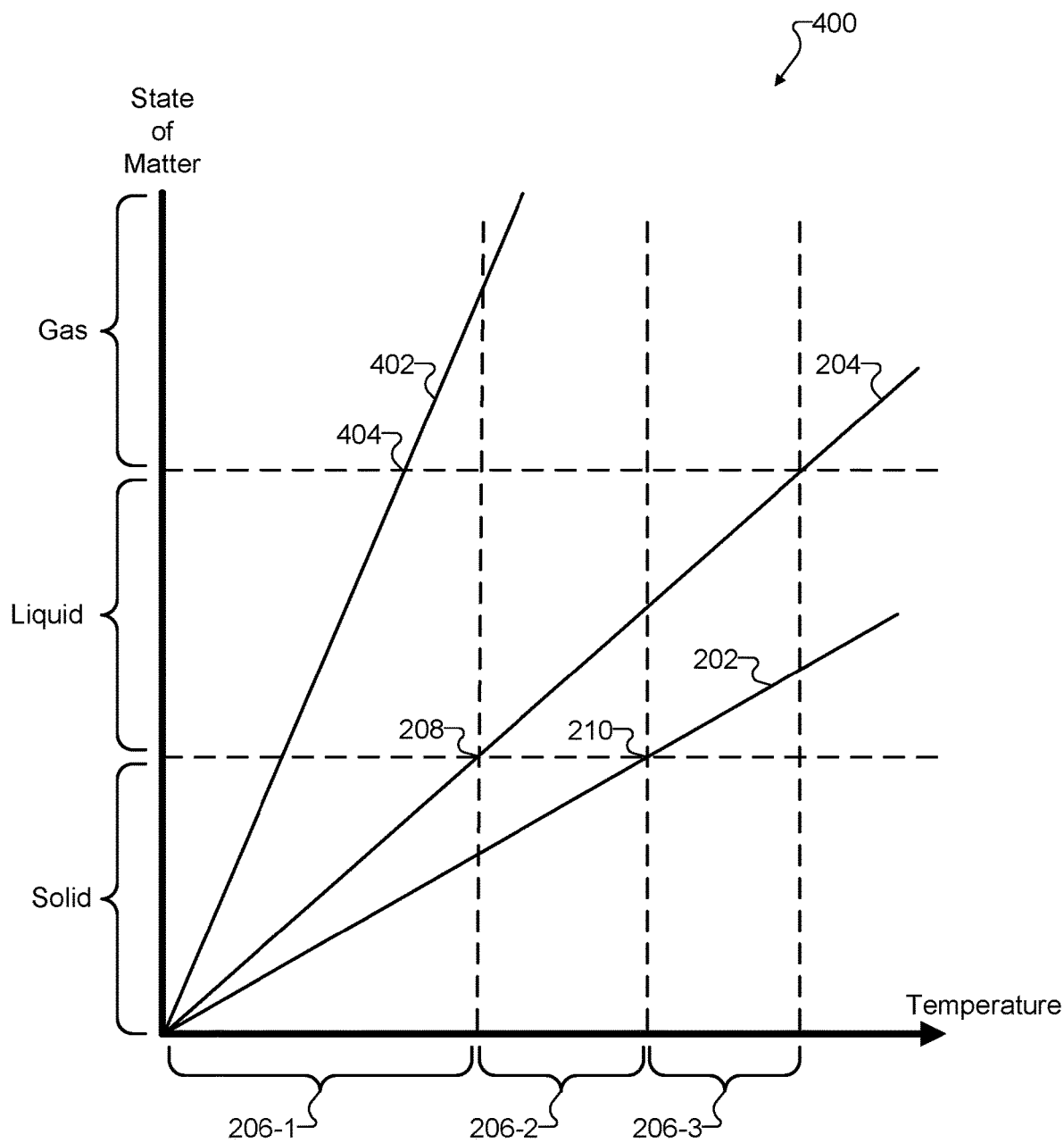
FIG. 4 illustrates an exemplary temperature-state profile for the insulative material of FIGS. 3A-3B alongside the temperature-state profiles of the conductive materials illustrated in FIG. 2 according to principles described herein.

FIG. 4 illustrates an exemplary temperature-state profile 402 for insulative material 300 alongside temperature-state profiles 202 and 204 of the conductive materials of wire 102 and pad 104, respectively, which were described above in relation to FIG. 2. As shown in a graph 400 of FIG. 4, insulative material 300 may have a boiling point 404 at a lower temperature than, for example, the temperature of melting point 208 at which pad 104 reflows. Accordingly, by heating contact area 106 of pad 104 and segment 110-1 of wire 102 (including the insulative material 300 that covers it) to a temperature within temperature region 206-2 to form connection joint 100 as described above, the insulative material 300 sheathing segment 110-1 will automatically burn off or vaporize during the process.

Non-fusion-based connection joints such as connection joint 100 may be used in any of various applications where dissimilar materials (e.g., conductive materials) are joined to one another. For instance, in some examples, such connection joints may be used for medical devices configured to be implanted within a patient.

As mentioned above, a medical device configured to be implanted within a patient may include electronic circuitry, a housing enclosing the electronic circuitry and that is biocompatible and hermetically sealed, and a feedthrough assembly of the housing including one or more vias upon which corresponding one or more pads are disposed external to the housing. The feedthrough assembly may be configured to conduct (e.g., by way of the vias) electrical signals to and from the electronic circuitry enclosed within the housing and one or more electrodes included on an electrode lead coupled with the medical device by way of the one or more pads. For example, the electrode lead may be associated with (e.g., may include) one or more wires each constructed from a first conductive material having a first melting point. The pads, meanwhile, may be constructed from a second conductive material different from the first conductive material and having a second melting point lower than the first melting point. The first and second conductive materials from which the wires and pads are constructed may be biocompatible so as to be suitable for inclusion within the medical device.

As illustrated and described above, connection joints such as connection joint 100 may be formed between respective wires and pads included in the one or more wires of the electrode lead and the one or more pads associated with the feedthrough assembly of the implantable medical device. Specifically, respective cavities may be formed in each pad by a displacement of the second conductive material that occurs when a particular wire (e.g., a particular segment of the wire) is in contact with the pad at a contact area of the pad that is heated to a temperature between the first and second melting points so as to reflow the second conductive material without reflowing the first conductive material. Then, respective fixatives may be applied to cover each connection joint so as to fix the respective segments of each wire in place within the respective cavities of each pad. As with the first and second conductive materials (as well as an insulative material that may sheath one or more of the wires included in the electrode lead), the fixative may be a non-conductive and biocompatible fixative suitable for inclusion within the medical device.

One example of a medical device that may employ connection joints formed in this way may be a cochlear implant included within a cochlear implant system. In this example, an electrode lead included within the cochlear implant system may thus be configured to couple to the cochlear implant (e.g., using a feedthrough assembly comprising a plurality of connection joints as described above) at a proximal tip of the electrode lead. The electrode lead may also be configured to be inserted into a cochlea of the patient at a distal tip of the electrode lead in order to apply electrical stimulation generated by the cochlear implant to the cochlea of the patient.

Figure 5:
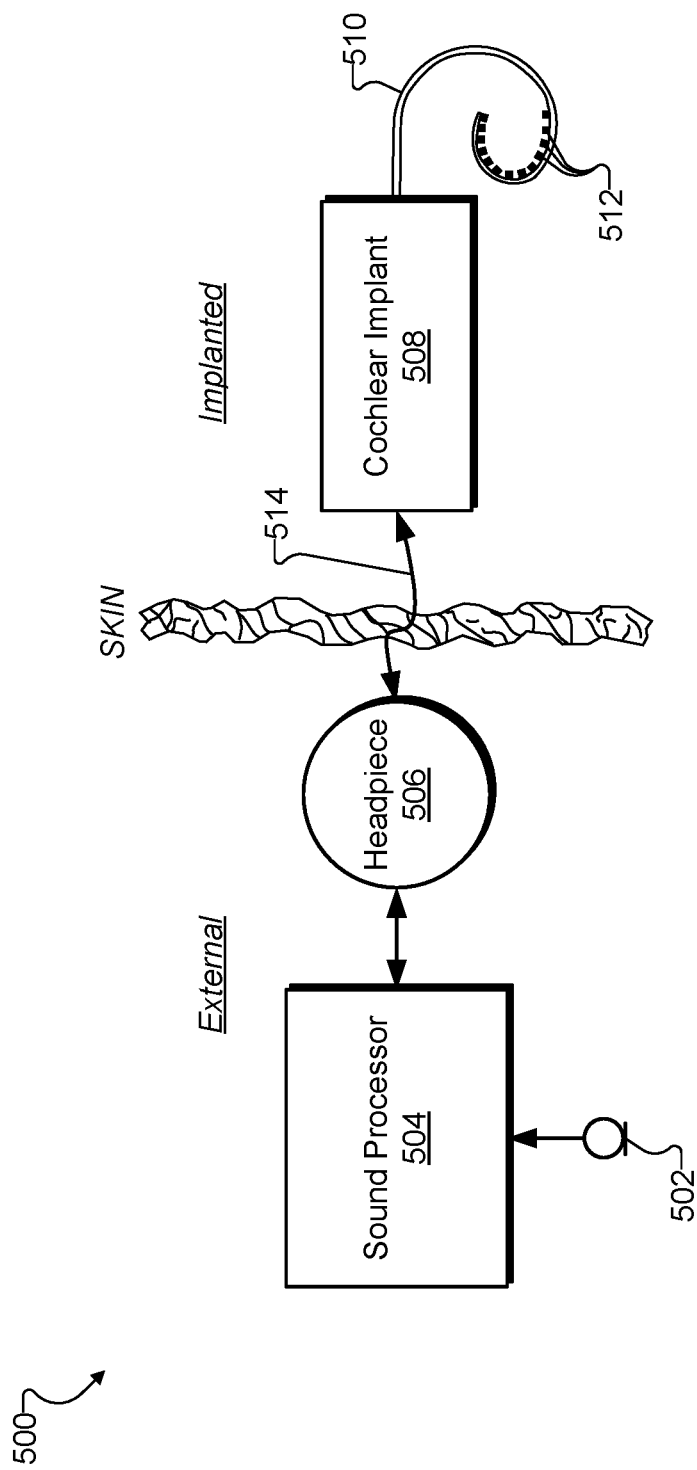
FIG. 5 illustrates an exemplary cochlear implant system that may make use of connection joints such as the connection joint of FIG. 1D according to principles described herein.

To illustrate, FIG. 5 shows an exemplary cochlear implant system 500 that may make use of connection joints such as connection joint 100 described above. As shown, cochlear implant system 500 may include a microphone 502, a sound processor 504, a headpiece 506 having a coil disposed therein, a cochlear implant 508, and an electrode lead 510. As will be described and illustrated in more detail below, electrode lead 510 may include a plurality of wires for coupling an array of electrodes 512 disposed on a distal portion of electrode lead 510 to cochlear implant 508 by way of a feedthrough assembly or the like. The distal portion of electrode lead 510 including electrodes 512 may be configured to be inserted into the cochlea to stimulate the cochlea after the distal portion of electrode lead 510 is inserted into the cochlea. It will be understood that one or more other electrodes (e.g., including a ground electrode, not explicitly shown) may also be disposed on other parts of electrode lead 510 (e.g., on a proximal portion of electrode lead 510). As shown, electrode lead 510 may be pre-curved so as to properly fit within the spiral shape of the cochlea. Additional or alternative components may be included within cochlear implant system 500 as may serve a particular implementation.

Microphone 502 may be configured to detect audio signals presented to the user. Microphone 502 may be implemented in any suitable manner. For example, microphone 502 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 504. Additionally or alternatively, microphone 502 may be implemented by one or more microphones disposed within headpiece 506, one or more microphones disposed within sound processor 504, one or more beam-forming microphones, and/or any other suitable microphone as may serve a particular implementation.

Sound processor 504 may be configured to process an audio signal (e.g., an acoustic audio signal detected by microphone 502, an electrical audio signal input by way of an auxiliary audio input port or a Clinician's Programming Interface ("CPI") device, etc.) and to direct stimulation representative of the audio signal to be presented to a user of cochlear implant system 500. For example, the stimulation representative of the audio signal and directed by sound processor 504 to be presented to the patient may be electrical stimulation presented by way of cochlear implant 508 and electrode lead 510 implanted within the user, as will be described below.

Sound processor 504 may be configured to direct cochlear implant 508 to generate and apply electrical stimulation (also referred to herein as "stimulation current") representative of an audio signal to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 504 may process the audio signal in accordance with a selected sound processing strategy or program to generate appropriate stimulation parameters for controlling cochlear implant 508. Sound processor 504 may be housed within any suitable housing such as a behind-the-ear ("BTE") unit, a body worn unit, or the like.

In some examples, sound processor 504 may wirelessly transmit stimulation parameters (e.g., in the form of data words included in a forward telemetry sequence) and/or power to cochlear implant 508 by way of a wireless communication link 514 between headpiece 506 and cochlear implant 508 (e.g., a wireless link between a coil disposed within headpiece 506 and a coil included within or coupled to cochlear implant 508). To this end, headpiece 506 may be communicatively coupled to sound processor 504 and may include an antenna (e.g., a coil and/or one or more wireless communication components) configured to facilitate selective wireless coupling of sound processor 504 to cochlear implant 508. Headpiece 506 may be configured to be affixed to the patient's head and positioned or aligned such that an antenna housed within headpiece 506 is communicatively coupled to a corresponding implantable antenna (which may also be implemented by a coil and/or one or more wireless communication components) included within or otherwise associated with cochlear implant 508. In this manner, stimulation parameters and/or power signals may be wirelessly transferred between sound processor 504 and cochlear implant 508 via wireless communication link 514.

Cochlear implant 508 may include any type of implantable stimulator that may be used in association with the systems and methods described herein. For example, cochlear implant 508 may be implemented by an implantable cochlear stimulator. In some alternative implementations, cochlear implant 508 may include a brainstem implant and/or any other type of cochlear implant that may be implanted within a patient and configured to apply stimulation to one or more stimulation sites located along an auditory pathway of a patient.

In some examples, cochlear implant 508 may be configured to generate electrical stimulation representative of an audio signal processed by sound processor 504 (e.g., an audio signal detected by microphone 502) in accordance with one or more stimulation parameters transmitted thereto by sound processor 504. Electronic circuitry included within cochlear implant 508 (e.g., circuitry for generating electrical stimulation, etc.) may be coupled to electrodes 512 external to cochlear implant 508 by way of a feedthrough assembly that facilitates electrical signaling through a hermetic seal of cochlear implant 508, as will be described and illustrated in more detail below. By way of the feedthrough assembly, cochlear implant 508 may be configured to apply the electrical stimulation to one or more stimulation sites (e.g., one or more intracochlear regions) within the patient via electrodes 512 disposed along electrode lead 510. In some examples, cochlear implant 508 may include (e.g., within the electronic circuitry described above) a plurality of independent current sources each associated with a channel defined by one or more of electrodes 512. In this manner, different stimulation current levels may be applied to multiple stimulation sites simultaneously by way of multiple electrodes 512.

Figure 6:
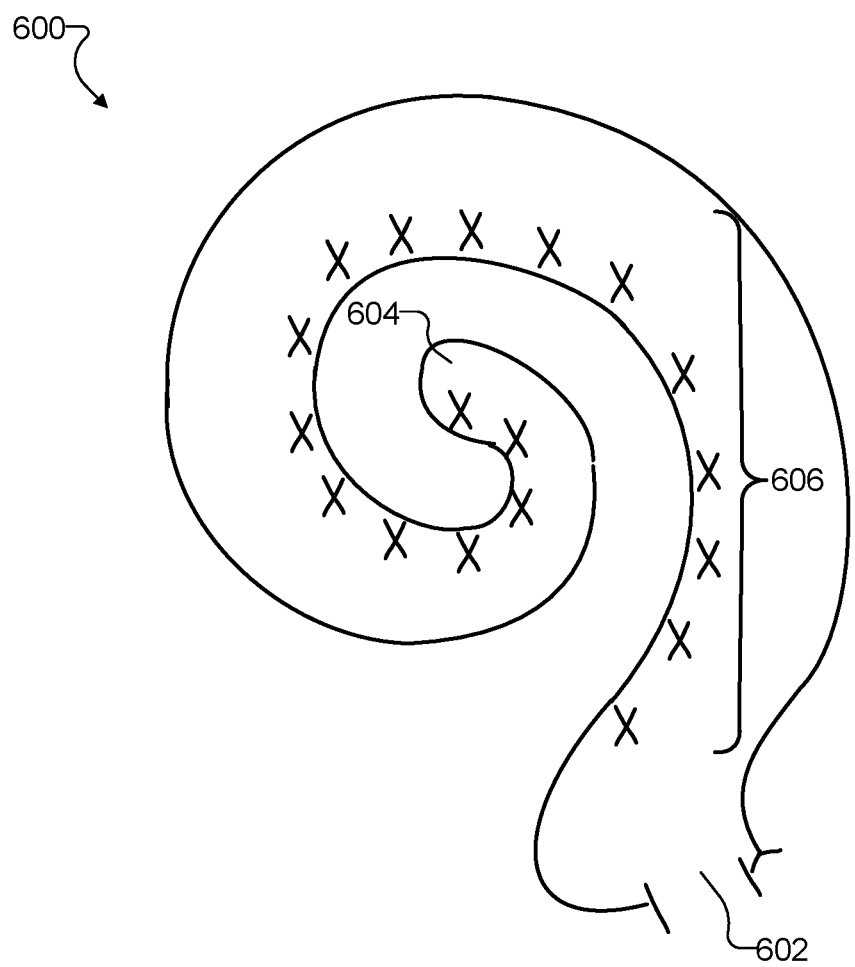
FIG. 6 illustrates a schematic structure of an exemplary human cochlea according to principles described herein.

FIG. 6 illustrates a schematic structure of the human cochlea 600 into which electrode lead 510 may be inserted. As shown in FIG. 6, cochlea 600 is in the shape of a spiral beginning at a base 602 and ending at an apex 604. Within cochlea 600 resides auditory nerve tissue 606, which is denoted by Xs in FIG. 6. The auditory nerve tissue 606 is organized within cochlea 600 in a tonotopic manner. Relatively low frequencies are encoded at or near the apex 604 of the cochlea 600 (referred to as an "apical region") while relatively high frequencies are encoded at or near the base 602 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

Figure 7B:
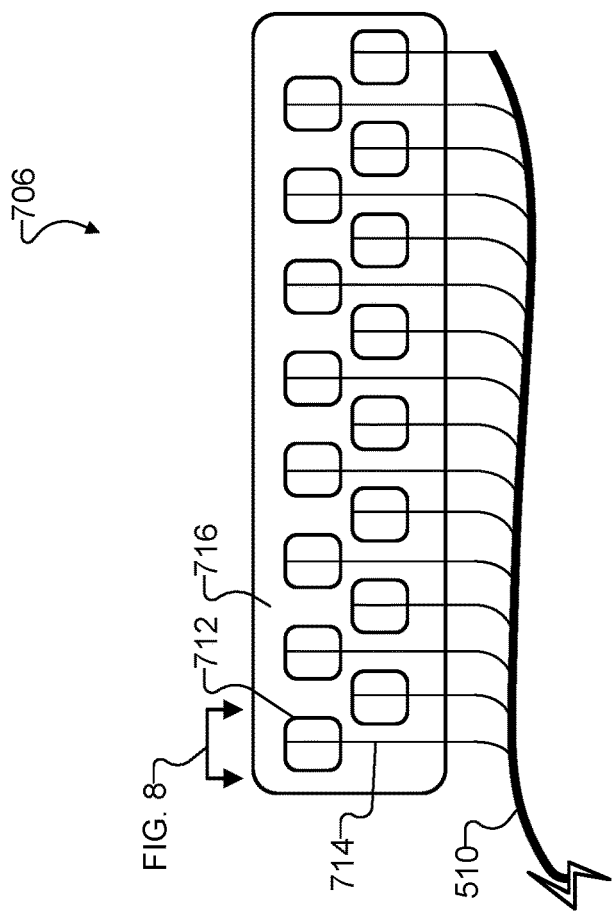
FIGS. 7A-7B illustrate various components of the cochlear implant and the electrode lead included in the cochlear implant system of FIG. 5 according to principles described herein.
Figure 7A:
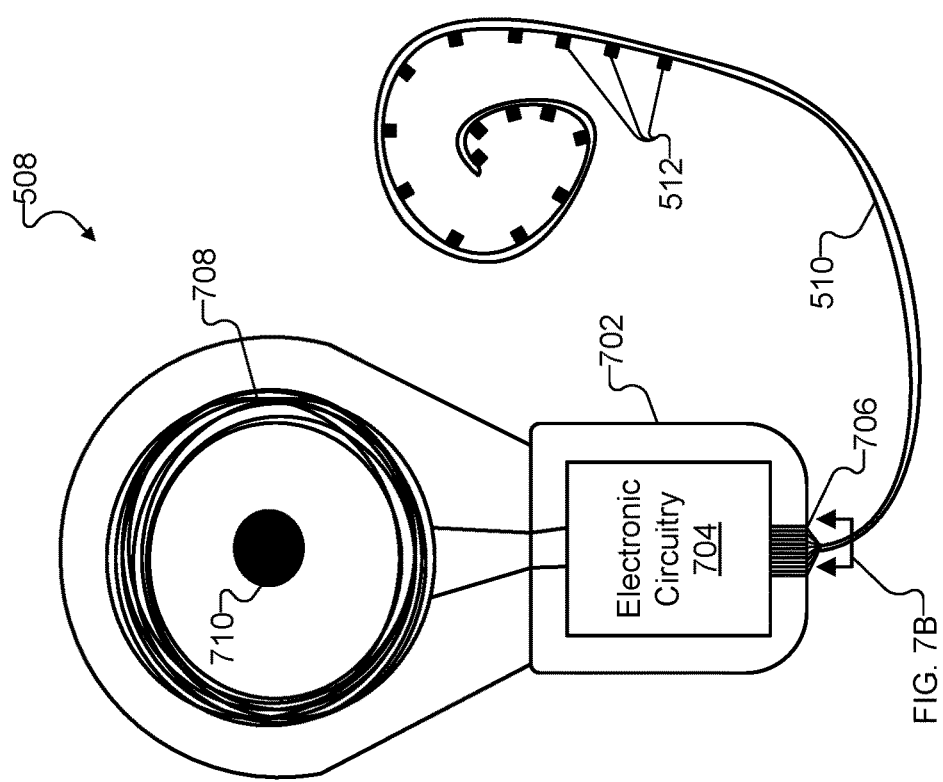

FIGS. 7A-7B illustrate various components of cochlear implant 508 and electrode lead 510 of cochlear implant system 500. Specifically, as shown in FIG. 7A, cochlear implant 508 may include a housing 702 in which electronic circuitry 704 may be housed. Electronic circuitry 704 may be configured to generate electrical stimulation that is applied to various areas of the cochlea of the patient by way of electrodes 512 on electrode lead 510, as well as to perform various other operations described above such as communicating with sound processor 504 located external to the patient (not shown in FIGS. 7A and 7B). As such, housing 702 may be biocompatible (i.e., safe for implantation in the human body and resistant to deterioration by bodily tissue, fluids, and/or processes occurring at the implantation site). Along the same lines, housing 702 may be hermetically sealed to ensure that electronic circuitry 704 (which may not be equally biocompatible or designed to operate when surrounded by bodily fluids and tissue) does not come into contact with the fluids and/or tissue at the implantation site.

While electronic circuitry 704 may be hermetically sealed off from the environment outside of housing 702, proper operation of cochlear implant 508 may require electronic circuitry 704 to be communicatively coupled with certain components implanted within the patient but external to housing 702. To this end, housing 702 may include one or more feedthrough assemblies configured to conduct communication signals, power, and/or other electrical signals to and from electronic circuitry 704 within housing 702. For example, as shown in FIG. 7A at the bottom of housing 702 and in FIG. 7B as a closeup straight-on view, a feedthrough assembly 706 may be associated with (e.g., included on) housing 702. Additionally, one or more other feedthrough assemblies or other means of passing electrical signals to and from electronic circuitry 704 through housing 702 may be employed to allow cochlear implant 508 to couple with external sound processor 504. For example, as described above, electronic circuitry 704 may send and/or receive communicative signals and/or power to and from sound processor 504 by way of an antenna coil 708 that may be wirelessly and communicatively coupled with a corresponding antenna coil in headpiece 506 when a magnet 710 engages with a corresponding magnet in headpiece 506 or when the headpiece is otherwise aligned with cochlear implant 508.

Feedthrough assembly 706 may be configured to conduct electrical signals to and from electronic circuitry 704 enclosed within housing 702 and electrodes 512 included on electrode lead 510 by way of one or more vias that form part of the hermetic seal of housing 702 while also carrying electrical signals in a controlled manner from inside housing 702 to outside housing 702 or vice versa. For example, vias included within feedthrough assembly 706 may be constructed from a biocompatible conductive material such as platinum, a platinum alloy, or another such material as may serve a particular implementation. An external pad constructed of another conductive and biocompatible material (e.g., the same material as the via in certain examples) may be associated with each via such as by being integrated into the via as part of the via, disposed on the external surface of the via, or the like. Similarly, an internal pad may be similarly disposed on the internal surface of the via.

FIG. 7B illustrates a plurality of external pads included on feedthrough assembly 706, including a pad 712. Also shown in FIG. 7B are a plurality of wires associated with electrode lead 510, including a wire 714. The pads of feedthrough assembly and their respective vias are shown to be separated by an insulative material 716 (e.g., a biocompatible, non-conductive ceramic material or the like).

Each of the wires, including wire 714, may be electrically coupled with one of electrodes 512, and may also be joined with one of the pads of feedthrough assembly 706 so as to be conductively coupled through housing 702 to electronic circuitry 704. For example, as shown, wire 714 may be joined to pad 712. In examples where the pads (e.g., including pad 712) and the wires (e.g., including wire 714) are constructed from different materials, the respective connection joints between the wires and pads may be non-fusion-based connection joints such as connection joint 100.

Figure 8:
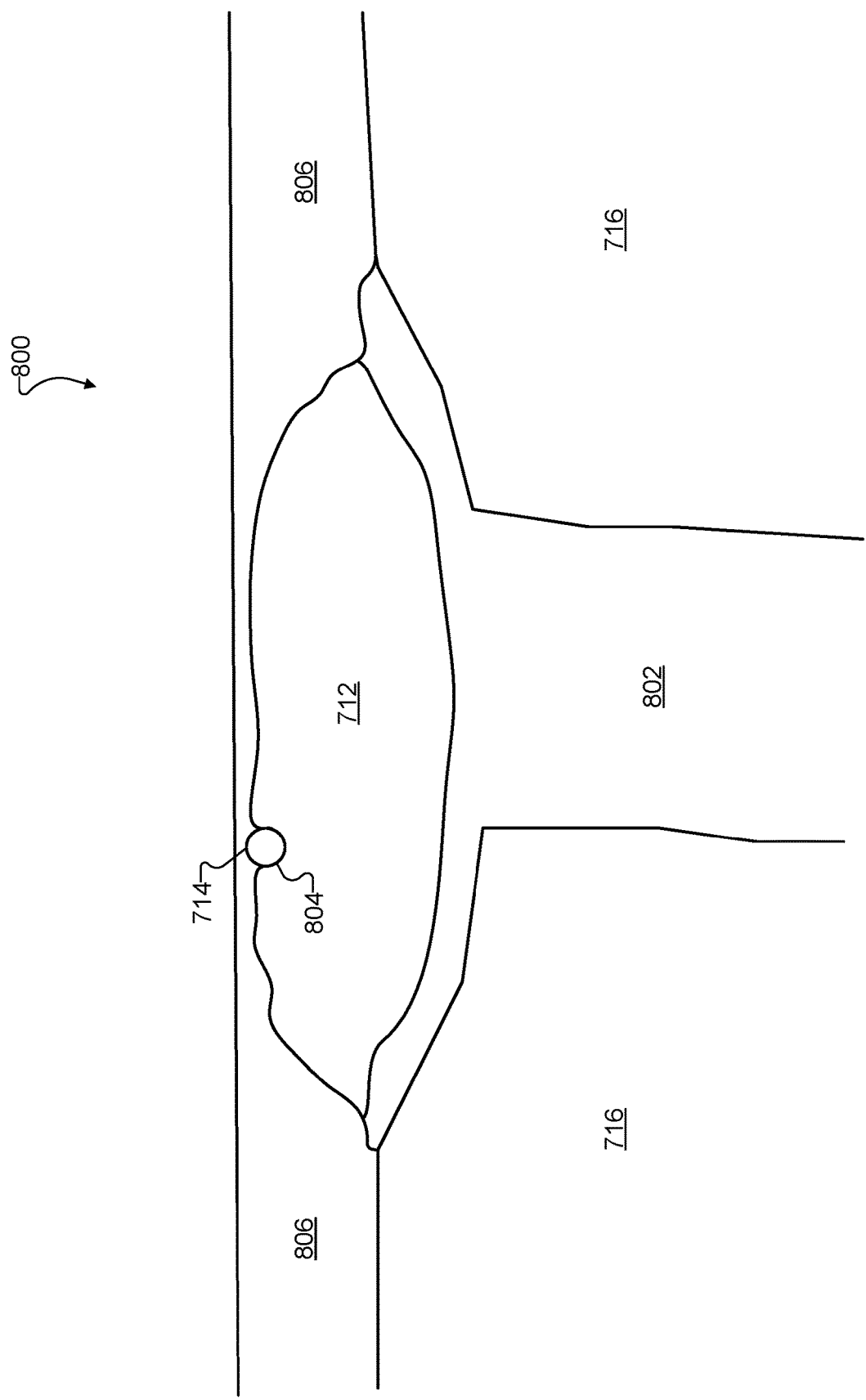
FIG. 8 illustrates a cross-sectional view of an exemplary connection joint disposed on an exemplary via joining one of the wires illustrated in FIG. 7B and one of the pads illustrated in FIG. 7B according to principles described herein.

To illustrate, FIG. 8 shows a cross-sectional view of an exemplary connection joint 800 disposed on an exemplary via and that joins wire 714 and pad 712. Specifically, in FIG. 8, insulative material 716 of feedthrough assembly 706 is shown to surrounds a via 802 that is configured to carry electrical signals through feedthrough assembly while maintaining a hermetic seal for housing 702 to keep fluids from seeping in to housing 702. As shown, pad 712 is disposed on top of via 802 (i.e., on the side external to housing 702), and it will be understood that another similar pad may also be disposed on an opposite side of via 802 (i.e., on the side internal to housing 702) so that wires associated with electronic circuitry 704 may be joined thereto (not explicitly shown).

In accordance with the operations described above in relation to connection joint 100, a contact area where wire 714 is positioned may be heated sufficiently to reflow at least some of the conductive material from which pad 712 is constructed (while also being heated insufficiently to reflow wire 714) such that wire 714 may displace some of the conductive material of pad 712 to form a groove 804. After pad 712 has cooled to a solid state, a fixative 806 is applied to cover wire 714, pad 712, and parts of insulative material 716. As described above, fixative 806 may fix the segment of wire 714 touch pad 712 in place within groove 804. Once fixative 806 has been properly cured so as to hold wire 714 rigidly in place within groove 804, a continuity test may be performed from, for example, the bottom of via 802 (not explicitly shown) to an electrode 512 associated with (e.g., conductively coupled with) wire 714.

Figure 9:
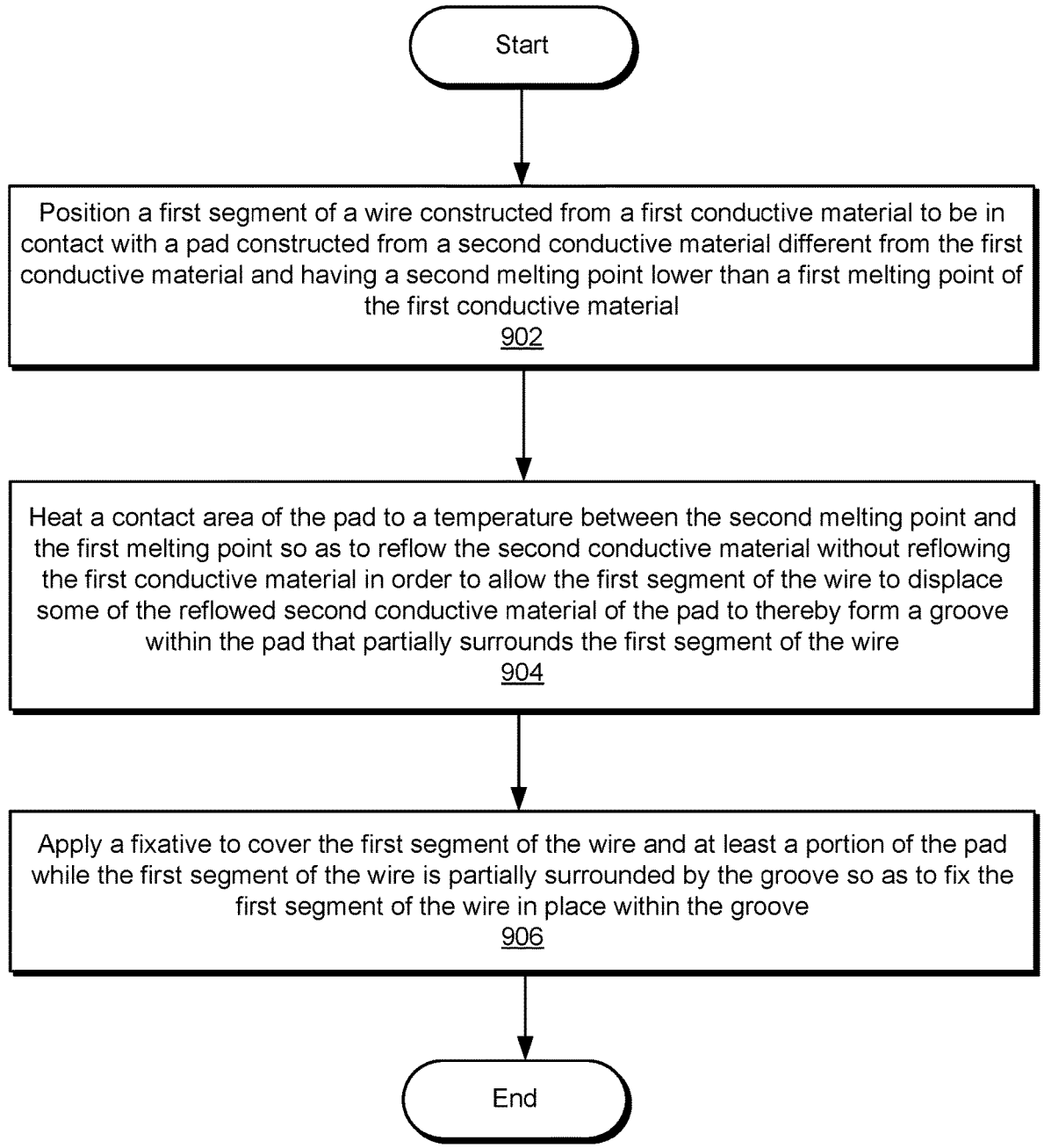
FIG. 9 illustrates an exemplary method for making a connection joint for joining a wire and a pad constructed of different conductive materials according to principles described herein.

FIG. 9 illustrates an exemplary method 900 for making a connection joint for joining a wire and a pad constructed of different conductive materials. One or more of the operations shown in FIG. 9 may be performed by a person (e.g., a welding technician), a machine (e.g., a robotic welding system), or any other suitable actor using any suitable equipment (e.g., including equipment described herein) as may serve a particular implementation. While FIG. 9 illustrates exemplary operations according to one embodiment, other embodiments may omit, add to, reorder, and/or modify any of the operations shown in FIG. 9.

In operation 902, an actor performing method 900 may position a first segment of a wire to be in contact with a pad at a contact area of the pad. In some examples, the wire may be constructed from a first conductive material, while the pad may be constructed from a second conductive material different from the first conductive material. For example, the second conductive material may have a second melting point lower than a first melting point of the first conductive material. Operation 902 may be performed in any of the ways described herein.

In operation 904, the actor performing method 900 may heat the contact area of the pad to a temperature between the second melting point and the first melting point. For example, the contact area may be heated while the first segment of the wire is in contact with the pad at the contact area in accordance with the positioning of operation 902. By heating the contact area to the temperature between the second and first melting points in operation 904, the second conductive material from which the pad is constructed may reflow without the first conductive material from which the wire is constructed also reflowing. As such, the reflowing of the second conductive material may allow the first segment of the wire to displace some of the reflowed second conductive material of the pad to thereby form a groove within the pad that partially surrounds the first segment of the wire. Operation 904 may be performed in any of the ways described herein.

In operation 906, the actor performing method 900 may apply a fixative to cover the first segment of the wire and at least a portion of the pad so as to fix the first segment of the wire in place within the groove. For example, the fixative may be applied subsequent to the heating of operation 904 and while the first segment of the wire is partially surrounded by the groove. Operation 906 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A connection joint comprising:
    a wire associated with an electrode lead external to a biocompatible and hermetically sealed housing of a medical device configured to be implanted within a patient, the wire constructed from a first conductive material having a first melting point;
    a pad disposed external to the housing of the medical device on a via of a feedthrough assembly of the housing, wherein:
        the feedthrough assembly is configured to conduct, by way of the via, electrical signals to and from electronic circuitry enclosed within the housing and an electrode included on the electrode lead,
        the wire is coupled with the medical device by way of the pad, and
        the pad is constructed from a second conductive material different from the first conductive material and having a second melting point lower than the first melting point;
    a groove that is within the pad and that partially surrounds a first segment of the wire, the groove formed by a displacement of the second conductive material that occurs when both
        the first segment of the wire is in contact with the pad at a contact area of the pad, and
        the contact area is heated to a temperature between the second melting point and the first melting point so as to reflow the second conductive material from which the pad is constructed without reflowing the first conductive material from which the wire is constructed; and
    a fixative covering the first segment of the wire and at least a portion of the pad so as to fix the first segment of the wire in place within the groove.

2. The connection joint of claim 1, wherein:
    prior to the groove being formed by the heating of the contact area and while the first segment of the wire is in contact with the pad at the contact area, the first segment of the wire and a second segment of the wire adjacent to the first segment are both sheathed by an insulative material having a boiling point lower than the temperature to which the contact area is heated;
    when the groove is formed by the heating of the contact area, the insulative material is burned off of the first segment of the wire without being burned off of the second segment of the wire; and
    subsequent to the groove being formed by the heating of the contact area, the first segment of the wire partially surrounded by the groove is not sheathed by the insulative material while the second segment of the wire adjacent to the first segment continues to be sheathed by the insulative material.

3. The connection joint of claim 2, wherein the insulative material is a chemical vapor deposited polymer.

4. The connection joint of claim 1, wherein:
    the first and second conductive materials are biocompatible so as to be suitable for inclusion within the medical device; and
    the fixative is a non-conductive and biocompatible epoxy suitable for inclusion within the medical device.

5. The connection joint of claim 4, wherein:
    the first conductive material is a platinum-iridium alloy material; and
    the second conductive material is a pure platinum material.

6. The connection joint of claim 1, wherein the medical device is a cochlear implant included within a cochlear implant system and the electrode lead is an electrode lead included within the cochlear implant system and configured to couple to the cochlear implant at a proximal tip of the electrode lead and to be inserted into a cochlea of the patient at a distal tip of the electrode lead in order to apply electrical stimulation generated by the cochlear implant to the cochlea of the patient.

7. The connection joint of claim 1, wherein the groove within the pad is formed by applying pressure, while the contact area is heated to the temperature and the second conductive material is reflowed, onto the first segment of the wire to force the first segment of the wire to partially sink into the reflowed second conductive material of the pad so as to displace some of the reflowed second conductive material to form the groove within the pad; and allowing, subsequent to the contact area being heated and prior to the fixative being applied, the second conductive material of the pad to cool until the second conductive material is no longer reflowed;

wherein the fixative is applied in a liquid form and subsequently cured to change from the liquid form into a solid form.

8. A medical device configured to be implanted within a patient, the medical device including:

electronic circuitry;

a housing enclosing the electronic circuitry and that is biocompatible and hermetically sealed; and a feedthrough assembly of the housing including a via upon which a pad is disposed external to the housing, the feedthrough assembly configured to conduct, by way of the via, electrical signals to and from the electronic circuitry enclosed within the housing and an electrode included on an electrode lead coupled with the medical device by way of the pad, the electrode lead including a wire constructed from a first conductive material having a first melting point and the pad constructed from a second conductive material different from the first conductive material and having a second melting point lower than the first melting point;

wherein a first segment of the wire is coupled to the pad by being partially surrounded by a groove within the pad, the groove formed by a displacement of the second conductive material that occurs when both the first segment of the wire is in contact with the pad at a contact area of the pad, and the contact area is heated to a temperature between the second melting point and the first melting point so as to reflow the second conductive material from which the pad is constructed without reflowing the first conductive material from which the wire is constructed, and covered by a fixative covering the first segment of the wire and at least a portion of the pad so as to fix the first segment of the wire in place within the groove.

9. The medical device of claim 8, wherein:

prior to the groove being formed by the heating of the contact area and while the first segment of the wire is in contact with the pad at the contact area, the first segment of the wire and a second segment of the wire adjacent to the first segment are both sheathed by an insulative material having a boiling point lower than the temperature to which the contact area is heated;

when the groove is formed by the heating of the contact area, the insulative material is burned off of the first segment of the wire without being burned off of the second segment of the wire; and subsequent to the groove being formed by the heating of the contact area, the first segment of the wire partially surrounded by the groove is not sheathed by the insulative material while the second segment of the wire adjacent to the first segment continues to be sheathed by the insulative material.

10. A method comprising:

positioning a first segment of a wire to be in contact with a pad at a contact area of the pad, wherein:

the wire is associated with an electrode lead external to a biocompatible and hermetically sealed housing of a medical device configured to be implanted within a patient, the wire is constructed from a first conductive material and is coupled with the medical device by way of the pad, the pad is disposed external to the housing of the medical device on a via of a feedthrough assembly of the housing, the pad is constructed from a second conductive material different from the first conductive material and having a second melting point lower than a first melting point of the first conductive material, and the feedthrough assembly is configured to conduct, by way of the via, electrical signals to and from electronic circuitry enclosed within the housing and an electrode included on the electrode lead;

heating, while the first segment of the wire is in contact with the pad at the contact area, the contact area of the pad to a temperature between the second melting point and the first melting point so as to reflow the second conductive material from which the pad is constructed without reflowing the first conductive material from which the wire is constructed, the reflowing of the second conductive material allowing the first segment of the wire to displace some of the reflowed second conductive material of the pad to thereby form a groove that is within the pad and that partially surrounds the first segment of the wire; and applying, subsequent to the heating and while the first segment of the wire is partially surrounded by the groove, a fixative to cover the first segment of the wire and at least a portion of the pad so as to fix the first segment of the wire in place within the groove.

11. The method of claim 10, wherein:

prior to the heating of the contact area and while the first segment of the wire is positioned to be in contact with the pad at the contact area, the first segment of the wire and a second segment of the wire adjacent to the first segment are both sheathed by an insulative material having a boiling point lower than the temperature to which the contact area is heated;

during the heating of the contact area to form the groove, the insulative material is burned off of the first segment of the wire without being burned off of the second segment of the wire; and subsequent to the heating of the contact area to form the groove, the first segment of the wire partially surrounded by the groove is not sheathed by the insulative material while the second segment of the wire adjacent to the first segment continues to be sheathed by the insulative material.

12. The method of claim 11, wherein the insulative material is a chemical vapor deposited polymer.

13. The method of claim 10, wherein:

the first and second conductive materials are biocompatible so as to be suitable for inclusion within the medical device; and the fixative is a non-conductive and biocompatible epoxy suitable for inclusion within the medical device.

14. The method of claim 13, wherein:
the first conductive material is a platinum-iridium alloy material; and
the second conductive material is a pure platinum material.

15. The method of claim 10, wherein the medical device is a cochlear implant included within a cochlear implant system and the electrode lead is an electrode lead included within the cochlear implant system and configured to couple to the cochlear implant at a proximal tip of the electrode lead and to be inserted into a cochlea of the patient at a distal tip of the electrode lead in order to apply electrical stimulation generated by the cochlear implant to the cochlea of the patient.

16. The method of claim 10, further comprising:
applying pressure, during the heating of the contact area and while the second conductive material is reflowed, onto the first segment of the wire to force the first segment of the wire to partially sink into the reflowed second conductive material of the pad so as to displace some of the reflowed second conductive material to form the groove within the pad; and
allowing, subsequent to the heating of the contact area and prior to the applying of the fixative, the second conductive material of the pad to cool until the second conductive material is no longer reflowed;
wherein the applying of the fixative includes
applying the fixative in a liquid form, and
curing the fixative, subsequent to the applying of the fixative in the liquid form, to change the fixative from the liquid form into a solid form.

17. The medical device of claim 9, wherein the insulative material is a chemical vapor deposited polymer.

18. The medical device of claim 8, wherein:
the first and second conductive materials are biocompatible so as to be suitable for implantation within the patient; and
the fixative is a non-conductive and biocompatible epoxy suitable for implantation within the patient.

19. The medical device of claim 8, wherein:
the first conductive material is a platinum-iridium alloy material; and
the second conductive material is a pure platinum material.

20. The medical device of claim 8, wherein the medical device is a cochlear implant included within a cochlear implant system and the electrode lead is an electrode lead included within the cochlear implant system and configured to couple to the cochlear implant at a proximal tip of the electrode lead and to be inserted into a cochlea of the patient at a distal tip of the electrode lead in order to apply electrical stimulation generated by the cochlear implant to the cochlea of the patient.

* * * * *